(12) United States Patent
Sadee et al.

(10) Patent No.: US 9,441,275 B2
(45) Date of Patent: Sep. 13, 2016

(54) POLYMORPHISM IN CYP3A4 GENE AFFECTING DRUG METABOLIZING AND USES THEREOF

(75) Inventors: Wolfgang Sadee, Upper Arlington, OH (US); Danxin Wang, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 61 days.

(21) Appl. No.: 13/259,514

(22) PCT Filed: Mar. 26, 2010

(86) PCT No.: PCT/US2010/028842
§ 371 (c)(1),
(2), (4) Date: Oct. 7, 2011

(87) PCT Pub. No.: WO2010/111600
PCT Pub. Date: Sep. 30, 2010

(65) Prior Publication Data
US 2012/0040347 A1    Feb. 16, 2012

Related U.S. Application Data

(60) Provisional application No. 61/163,555, filed on Mar. 26, 2009.

(51) Int. Cl.
| | | |
|---|---|---|
| C12P 19/34 | (2006.01) | |
| C12Q 1/68 | (2006.01) | |
| A01N 61/00 | (2006.01) | |
| G01N 33/50 | (2006.01) | |

(52) U.S. Cl.
CPC ......... *C12Q 1/6883* (2013.01); *G01N 33/5038* (2013.01); *C12Q 2600/106* (2013.01); *C12Q 2600/16* (2013.01); *C12Q 2600/172* (2013.01); *G01N 2800/044* (2013.01); *G01N 2800/52* (2013.01)

(58) Field of Classification Search
None
See application file for complete search history.

(56) References Cited

U.S. PATENT DOCUMENTS

| | | |
|---|---|---|
| 2003/0215819 A1 | 11/2003 | Frudakis |
| 2006/0073479 A1 | 4/2006 | Frudakis |
| 2008/0292584 A1 | 11/2008 | Roberts et al. |

FOREIGN PATENT DOCUMENTS

| | | |
|---|---|---|
| WO | 0120025 A2 | 3/2001 |
| WO | 2010111600 A1 | 9/2010 |

OTHER PUBLICATIONS

Hegele, Arterioscler. Thromb. Vasc. Biol. 2002, 22:1058-1061.*
PL Detail-Document 250801, Statin Dose Comparisons, Pharmacist's Letter/Prescribers Letter, May 2012, pp. 1-12.*
Gao (Eur J Clin Pharmacol, 2008, 64:877-882).*
PCT International Preliminary Report on Patentability, PCT/US2010/028842 filed Mar. 26, 2010, dated Oct. 6, 2011.
PCT International Search Report and the Written Opinion, PCT/US2010/28842 filed Mar. 26, 2010, dated Aug. 12, 2010.
GenBank, Reference SNP (refSNP) Cluster Report: rs 35599367, dated Dec. 20, 2008, Retrieved from the Internet:<URL:http://www.ncbi.nlm.nih.gov/projects/SNP/snp_ref.cgi?rs=35599367>, pp. 1-2.
Yamada, Y. et. al., "Genetic Risk for Metabolic Syndrome: Examination of Candidate Gene Polymorphisms Related to Lipid Metabolism in Japanese People," J. Med. Genet., Jan. 2008, pp. 22-28, vol. 45, No. 1.

* cited by examiner

*Primary Examiner* — Sarae Bausch
(74) *Attorney, Agent, or Firm* — Meunier Carlin & Curfman LLC

(57) ABSTRACT

A method for predicting a subject's risk factors for CYP3A4-related disorders includes detecting the allelic status of a SNP in a nucleic acid sample of the subject.

12 Claims, 3 Drawing Sheets
(1 of 3 Drawing Sheet(s) Filed in Color)

POLYMORPHISM IN CYP3A4 GENE AFFECTING DRUG METABOLIZING AND USES THEREOF

RELATED APPLICATIONS

This application claims priority to U.S. Provisional Patent Application 61/163,555 filed Mar. 26, 2009, the disclosure of which is incorporated herein by reference, in its entirety.

GOVERNMENT SUPPORT

This invention was made with government support under Grant Number NIH NIAID (1R21AI074399) awarded by the National Institutes of Health. The government has certain rights in the invention.

SEQUENCE LISTING

The instant application contains a Sequence Listing which has been submitted via EFS-Web and is hereby incorporated by reference in its entirety. The ASCII copy, created on Mar. 23, 2010, is named 604_50806_SEQLIST_OSURF-09032.txt and is 34,669 bytes in size.

BACKGROUND

Cytochrome P450 (CYP) enzymes metabolize endogenous and xenobiotic compounds. CYP3A4 belongs to the CYP3A subfamily and is the most abundant CYP enzyme. CYP3A4 is involved in metabolizing 45-60% of all currently used drugs (1), including several statins—cholesterol-lowering HMG-CoA reductase inhibitors. However, CYP3A4 activity shows wide inter-individual variation, influencing drug response and toxicity. While genetic factors are thought to be main contributors to inter-individual differences in CYP3A4 activity (2), currently known CYP3A4 polymorphisms cannot account for the observed variability.

Genetic variants in CYP3A4 that change the amino acid sequence are rare (<1%). A more common variant, CYP3A4*1B, in the 5'-flanking region, has been associated with drug response and diseases (3,4), but results are inconsistent (5-7), and its function remains controversial (3,8-10). Moreover, CYP3A4*1B is in linkage disequilibrium (LD) with the adjacent CYP3A5 (11), encoding a similar but usually less abundant CYP enzyme that could have accounted for any linked clinical phenotype (12).

Further suspected CYP3A4 polymorphisms include a TGT insertion (13), an enhancer region SNP (rs2737418) (14), and an intron7 SNP (rs4646437) (15). While reporter gene assays suggested an effect for the TGT insertion and for rs2737418, the in vivo significance of TGT remains unresolved (13), while results on CYP3A4 mRNA and enzyme activity were contradictory for rs2737418 (14). The intron7 SNP rs4646437 was found to be associated with CYP3A4 protein/enzyme activity, but only in livers from males (15). Therefore, the role of functional polymorphisms in CYP3A4 remains uncertain.

Single nucleotide polymorphisms (SNPs) are useful as biomarkers for predicting disease susceptibility or progression, or as a guide for individualized therapy, including drug therapy.

What are lacking are tools for predicting the likelihood that a particular patient will be responsive to a particular therapeutic agent, and in particular, identifying polymorphisms to which a CYP3A4 agent will be sensitive or resistant. Also lacking are tools for profiling genetic factors influencing sensitivity and resistance of patients to such therapeutic agents. Such tools, and the resulting gene expression profiles, would be predictive of treatment response of a patient to a particular drug, and would allow for increased predictability regarding efficacy, adverse drug reactions, chemosensitivity or chemoresistance of such patients to enable the design of optimal treatment regimens for patients, or to enable drug development in early clinical trials avoiding unexpected toxicities in poor metabolizers.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

SUMMARY

In a first aspect, there is provided herein a method for predicting a subject's response to CYP3A4-metabolized compounds, including, for example efficacy and/or adverse drug reactions. The method includes detecting the allelic status of one or more polymorphisms in a nucleic acid sample of the subject, wherein the polymorphism is one or more of: i) CYP3A4-associated SNP (rs35599367 [SEQ ID NO: 152]) located in intron6 (C>T); or, ii) a SNP in linkage disequilibrium therewith, wherein the allelic status of the polymorphism in the subject is predictive of the subject's risk for having or developing the CYP3A4-related disorder.

In another aspect, there is provided herein, a method of screening a subject for a prognostic biomarker of an CYP3A4-related disorder, comprising detecting the allelic status of one or more polymorphisms in a nucleic acid sample of the subject, wherein the polymorphism is one or more of: i) CYP3A4-associated SNP (rs35599367 [SEQ ID NO: 152]) located in intron6 (C>T); or, ii) a SNP in linkage disequilibrium therewith, wherein the allelic status of the polymorphism in the subject is predictive of the prognostic outcome of the CYP3A4-related disorder.

In certain embodiments, the method further includes the step of correlating the allelic status of the polymorphism in the subject with the allelic status of the polymorphism in a reference population to predict the subject's risk for having or developing the CYP3A4-related disorder.

In certain embodiment, the method further includes the step of correlating the allelic status of the polymorphism in the subject with the allelic status of the polymorphism in a reference population to predict whether the subject has a more or less severe phenotype of the CYP3A4-related disorder.

In certain embodiment, the method further includes the step of correlating the allelic status of the polymorphism in the subject with the allelic status of the polymorphism in a reference population to predict the prognostic outcome of the disorder in the subject.

In certain embodiment, the method further includes the step of correlating the allelic status of the polymorphism in the subject with the allelic status of the polymorphism in a reference population to predict the subject's response to treatment, dosage and/or toxicity.

In certain embodiment, the CYP3A4-related disorder comprises a metabolic-related disorder.

In certain embodiment, the CYP3A4-metabolized compounds comprise one or more pharmaceuticals metabolized in the liver, including statin drugs.

In certain embodiment, the CYP3A4-metabolized compounds comprise one or more of: CYP3A4 inhibitors or CYP3A4 enhancers.

In certain embodiment, the polymorphism comprises a CYP3A4-associated SNP (rs35599367 [SEQ ID NO: 152]) located in intron6 (C>T).

In certain embodiment, the polymorphism comprises rs35599367 [SEQ ID NO: 152], wherein the presence of the polymorphism in a subject is predictive of an increased risk for a CYP3A4-related disorder.

In certain embodiment, the presence of a minor allele of the polymorphism is predictive of lower levels of CYP3A4 in target tissue and is associated with a decreased CYP3A4 mRNA expression.

In another aspect, there is provided herein, a kit comprising an assay for detecting the allelic status of one or more polymorphisms in a nucleic acid sample of a subject, wherein the polymorphism is one or more of: i) a CYP3A4-associated SNP (rs35599367 [SEQ ID NO: 152]) located in intron6 (C>T); or, ii) a SNP in linkage disequilibrium therewith.

In certain embodiment, the kit further includes instructions for correlating the assay results with the subject's risk for having or developing a CYP3A4-related disorder.

In certain embodiment, the kit further includes instructions for correlating the assay results with the subject's prognostic outcome for the disorder.

In certain embodiment, the kit further includes instructions for correlating the assay results with the probability of success or failure of a particular drug treatment in the subject.

In another aspect, there is provided herein, a method for finding a functional polymorphism in a target gene implicated in an CYP3A4-related disorder, comprising: i) providing a sample of a target tissue expressing the target gene; ii) measuring the target gene's allelic mRNA expression imbalance (AEI) by: a) quantitatively measuring the relative amounts of mRNA generated from each of two alleles in a transcribed region of the target gene, and b) comparing the mRNA expression of one allele against the other allele to obtain an AEI ratio; and, iii) using the AEI ratio as a phenotype to scan the target gene for regions containing polymorphisms, wherein a significant association between the AEI ratio and the polymorphism indicates that the polymorphism is a functional polymorphism that can serve as a biomarker for the CYP3A4-related disorder.

In certain embodiment, the polymorphism resides in an intronic region.

In certain embodiment, the polymorphism is a SNP.

In certain embodiment, the biomarker affects gene transcription, mRNA processing, mRNA splicing, or a combination thereof.

In certain embodiment, the target gene is a CYP3A4 gene locus.

In another aspect, there is provided herein, a method for determining metabolism of a statin drug comprising screening for an intron6 SNP.

In another aspect, there is provided herein, a method for determining metabolism of a statin drug comprising screening for a CYP3A4-associated SNP (rs35599367 [SEQ ID NO: 152]) located in intron6 (C>T).

In another aspect, there is provided herein a biomarker for detecting variability in CYP3A4 comprising intron6 SNP.

In another aspect, there is provided herein a biomarker for detecting variability in CYP3A4 comprising a CYP3A4-associated SNP (rs35599367 [SEQ ID NO: 152]) located in intron6 (C>T).

In another aspect, there is provided herein, a biomarker for determining a dosing requirement of a CYP3A4-metabolizing therapeutic agent comprising SNP (rs35599367 [SEQ ID NO: 152]) located in intron6 (C>T).

In another aspect, there is provided herein a biomarker for determining a response of a CYP3A4-metabolizing therapeutic agent comprising SNP (rs35599367 [SEQ ID NO: 152]) located in intron6 (C>T).

In another aspect, there is provided herein a biomarker for determining toxicity of a CYP3A4-metabolizing therapeutic agent comprising SNP (rs35599367 [SEQ ID NO: 152]) located in intron6 (C>T). In certain embodiment, the therapeutic agent is a statin drug. In certain embodiment, the therapeutic agent is an anti-cancer drug. In certain embodiment, the therapeutic agent is a drug having a narrowly defined dosage regimen.

In another aspect, there is provided herein a method of clinical pharmacogenomic screening comprising: a) screening a sample for the presence of at least one or more biomarkers described herein, where the presence of the one or more biomarkers is indicative of a patient with altered metabolism; and b) including a reference control in a random or predetermined manner in the screening, wherein the reference control comprises DNA comprising a biomarker indicative of a patient with altered metabolism, wherein the detection of the presence of one or more biomarkers in one or more drug-metabolizing genes in the reference control verifies that the screening is effective to detect the same one or more biomarkers in one or more drug-metabolizing genes in the sample.

In another aspect, there is provided herein a method of personalized medical therapy, comprising: i) performing the method of screening described herein on samples from a target patient population to identify patients with a genetic profile comprising one or more mutations in the CYP3A4 or other gene associated with drug metabolism; and ii) treating patients identified in step i) as possessing a particular genetic profile with a therapy of interest particular to the identified genetic profile.

In certain embodiments, the genetic profile is indicative of a patient with altered metabolism.

In certain embodiments, the altered metabolism is selected from the group consisting of: poor metabolizer, intermediate metabolizer, extensive metabolizer, and ultra-rapid metabolizer.

In certain embodiments, the genetic profile is indicative of the effectiveness of the therapy of interest in the patient.

In certain embodiments, the genetic profile is indicative of a patient with a genetic disorder.

In certain embodiments, the genetic profile is indicative of a patient who should not be treated with a particular therapy.

In certain embodiments, the therapy of interest is used to treat a disease or disorder selected from the group consisting of: cancer, heart disease, neurological disorders, psychiatric disorders, autoimmune disorders, and metabolic disorders.

In certain embodiments, the one or more mutations comprises a mutation in CYP3A4 and wherein the therapy of interest comprises administration of at least one statin to the patient.

In another aspect, there is provided herein a method for identifying a cell that can be used to generate isolated genomic DNA suitable for use as a reference control, wherein the method comprises: a) prospectively screening a human volunteer for the presence of a human genomic DNA sequence comprising one or more polymorphisms in a nucleic acid sample of the volunteer associated with a genetic predisposition that determines a patient's predicted degree of response to a particular therapy; wherein the polymorphism is one or more of: i) CYP3A4-associated SNP (rs35599367 [SEQ ID NO: 152]) located in intron 6 (C>T); or, ii) a SNP in linkage disequilibrium therewith, wherein the allelic status of the polymorphism in the subject is predictive of the subject's risk for having or developing the CYP3A4-related disorder; b) isolating the cell from the volunteer that possesses the one or more mutations of interest; and c) subjecting DNA from the cell to a plurality of validated genomic screening assays.

BRIEF DESCRIPTION OF THE DRAWINGS

The patent or application file may contain at least one drawing executed in color. Copies of this patent or patent application publication with color drawing(s) will be provided by the Office upon request and payment of the necessary fee.

The invention can be more fully understood from the following detailed description, the drawings and the Sequence Descriptions that form a part of this application. The Sequence Descriptions and Sequence Listing attached hereto comply with the rules governing nucleotide and/or amino acid sequence disclosures in patent applications as set forth in 37 CFR §§1.821-1.825. The Sequence Descriptions contain the three letter codes for amino acids as defined in 37 CFR §§1.821-1.825, which are incorporated herein by reference.

DETAILED DESCRIPTION OF THE INVENTION

Figure 1A:
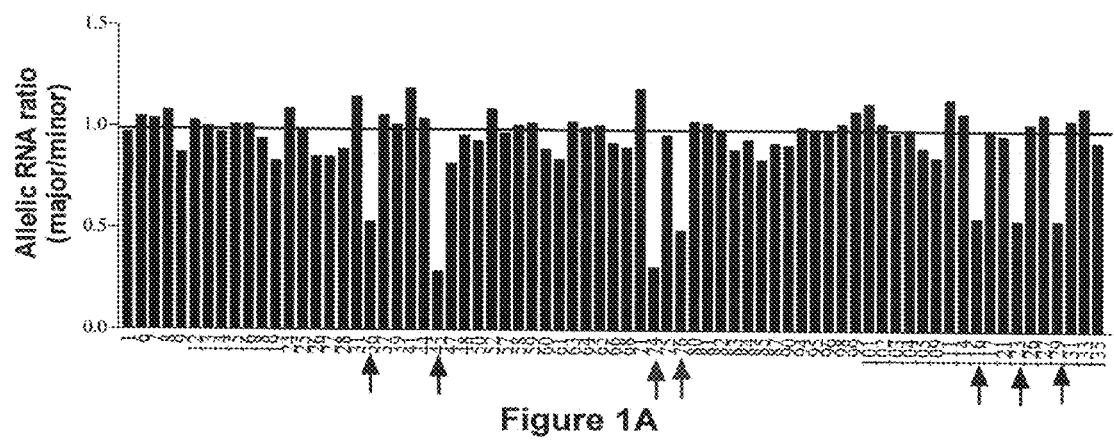
FIG. 1: Allelic mRNA/hnRNA expression ratios of CYP3A4 in human livers measured with a primer extension assay (SNaPshot) using multiple marker SNPs (FIG. 3) (FIG. 1A) or intron6 SNP rs35599367 [SEQ ID NO: 152] only (FIG. 1B). Allelic RNA ratios were normalized to gDNA ratios set at 1. Data represent the average of 2-3 measurement using single or multiple marker SNPs. An arrow indicates samples with AEI ratios significantly different from 1 (P<0.05). All allelic RNA ratios in Panel B are significantly different from 1 (ANOVA with Dunnett post-test, P<0.05).

The present invention will now be described with occasional reference to the specific embodiments of the invention. This invention may, however, be embodied in different forms and should not be construed as limited to the embodiments set forth herein. Rather, these embodiments are provided so that this disclosure will be thorough and complete, and will fully convey the scope of the invention to those skilled in the art.

All publications, patent applications, patents, and other references mentioned herein are incorporated by reference in their entirety. The disclosure of all patents, patent applications (and any patents that issue thereon, as well as any corresponding published foreign patent applications), Gen-Bank and other accession numbers and associated data, and publications mentioned throughout this description are hereby incorporated by reference herein. It is expressly not admitted, however, that any of the documents incorporated by reference herein teach or disclose the present invention.

The present invention may be understood more readily by reference to the following detailed description of the embodiments of the invention and the Examples included herein. However, before the present methods, compounds and compositions are disclosed and described, it is to be understood that this invention is not limited to specific methods, specific cell types, specific host cells or specific conditions, etc., as such may, of course, vary, and the numerous modifications and variations therein will be apparent to those skilled in the art. It is also to be understood that the terminology used herein is for the purpose of describing specific embodiments only and is not intended to be limiting.

In a broad aspect, the inventors herein found common polymorphisms in CYP3A4 by measuring allelic hnRNA/mRNA expression in human autopsy livers. A detectable allelic RNA expression imbalance (AEI) is a direct measure of cis-acting regulatory factors in CYP3A4 that affect RNA expression, processing, or turnover.

The results described herein demonstrate that an intron6 SNP of CYP3A4 fully accounts for the observed allelic mRNA expression pattern and correlates with CYP3A4 enzyme activity in human livers, while previously suggested polymorphisms had no effect.

Moreover, intron6 SNP was significantly associated with stable statin dosage taken for cholesterol control and with achievement of therapeutic LDL goal in a cohort of CAD patients.

EXAMPLE I

Methods:

Tissue samples. 133 liver autopsy/biopsy samples were obtained from The Cooperative Human Tissue Network Midwestern and Western Division, under a protocol approved by the Ohio State University Institutional Review Board (OSU IRB).

Patients. Subjects were participants in the Ohio State University Coronary Artery Disease Study, with patients presenting to the OSU Heart Center with symptomatic cardiovascular disease requiring PCI calls. 275 patients documented to be taking stable doses of a statin for lipid control were selected. Enrollment and trial conditions have been approved by the OSU IRB, with written informed consent obtained from each patient. The study population reflects demographics of the Columbus area and surrounding rural counties of Ohio.

DNA and RNA preparation. Preparation of genomic DNA, RNA and cDNA from tissues or blood samples were performed as described (16-18).

Quantitative analysis of allelic ratios in genomic DNA and RNA using SNaPshot. The detailed method has been published (16,17). Briefly, a fragment of DNA or RNA (after conversion to cDNA) surrounding a marker SNP was PCR amplified, followed by a primer extension assay (SNaPshot) that targets the polymorphic site. Seven marker SNPs located in either 3'UTR or intronic regions were used to measure allelic ratios of mature mRNA (3'UTR markers) or hnRNA (intronic markers) in 73 out of the 133 livers heterozygous for at least one marker SNP. Genomic DNA (gDNA) allelic ratios, normalized to 1, served as internal control; none of the subjects displayed gDNA copy number variants, detectable by a significant deviation from unity. Deviations of allelic RNA ratios from 1 (after normalization to DNA ratios), i.e., allelic expression imbalance (AEI), indicates the presence of cis-acting polymorphisms in CYP3A4 that affect mRNA expression levels.

Genotyping: Thirteen SNPs in CYP3A4 (including the 7 marker SNPs) were genotyped in gDNA from liver samples with a multiplex SNaPshot assay (19) or allele specific real-time PCR (20), as shown in Table 1.

TABLE 1

Polymorphisms tested in liver samples.

| SNP # | SNP ID | position |
|---|---|---|
| 1 | TGT ins | −11231 |
| 2 | rs2737418 G > T | −7310 |
| 3 | rs2740574 A > G (*1B) | −392 |
| 4 | rs2687105 A > T | intron 2 |
| 5 | rs28988579 T > G | intron 4 |
| 6 | rs35599367 C > T | intron 6 |
| 7 | rs2246709 C > T | intron 7 |
| 8 | rs4646437 C > T | Intron 7 |
| 9 | rs2242480G > A | intron10 |
| 10 | rs3735451A > G | intron 12 |
| 11 | rs28988604C > T | 3'UTR |
| 12 | rs28969391delT | 3'UTR |
| 13 | rs28371763A > T | 3'UTR |

Seven SNPs in CYP3A4/3A5 were genotyped in gDNA from 275 patients, as shown in Table 2.

TABLE 2

Polymorphisms tested in 275 patients.

| SNP ID | Gene | Position |
|---|---|---|
| TGT ins | CYP3A4 | Enhancer, −11231 |
| rs2740574 | CYP3A4 | Promoter, −392, *1B |
| rs35599367 | CYP3A4 | Intron 6 |
| rs4987161 | CYP3A4 | Exon 7 (F189S) |
| rs28371759 | CYP3A4 | Exon 10 (L293P) |
| rs776746 | CYP3A5 | Intron 3, *3 |
| rs41303343 | CYP3A5 | Exon 11, *7 |

PCR conditions and primer sequences are shown in Table 3, Table 4, Table 5.

Quantitative mRNA analysis of CYP3A4 and transcription factors PXR, RXRa, CAR, and HNF4a in human livers: mRNA levels were measured with real-time PCR (16,21) using gene-specific primers (22) (Table 3, Table 4, Table 5) and SYBR Green (Applied Biosystems), with GADPH mRNA as an internal control.

Table 3: Genotyping or AEI assays. Column labeled "Sequence of PCR primers and assay condition" discloses SEQ ID NOS 1-42, respectively, in order of appearance and column labeled "Primer extension primers and condition" discloses SEQ ID NOS 43-56, respectively, in order of appearance.

TABLE 3

Genotyping or AEI assays

| Snap shot assay | SNP# | rs# | location | Sequence of PCR primers and assay condition | Primer extension primers and condition |
|---|---|---|---|---|---|
| | 2 | rs2737418 | 7.3 kb upstream | F: GAACTTGCTGACCCTCTGCTTT [SEQ ID NO: 1] R: TAGCAAGCCACAGACAGCA [SEQ ID NO: 2] Choice Tag, 60° C. extension | CATTCTCCTTTAACCT GTTGACGA [SEQ ID NO: 43] 60° C. extension |
| | 3 | rs2740574 | promoter | F: AGAGCCATGACAGGGAATAAGACT AGA [SEQ ID NO: 3] R: TGGGCTATGTGCATGGAGCTT [SEQ ID NO: 4] JumpStart RedTag, 60° C. extension | AGGACAGCCATAGAG ACAAGGGCA [SEQ ID NO:44] 55° C. extension |
| | 5 | rs28988579 | intron 4 | F: TTTCCTTTCCAATCTGTATGCC [SEQ ID NO: 5] R: AAAGAACTGAAGGCTTCCCTC [SEQ ID NO: 6] Choice Tag, 60° C. extension | AGTATAATGTTGAGT AAATGTGGTGAAT [SEQ ID NO: 45] 55° C. extension |
| | 6 | rs35599367 | intron 6 | F: CTGAAGCACAGTGCTTACCCAT [SEQ ID NO: 7] R: GGTGCCAGTGATGCAGCT [SEQ ID NO: 8] Choice Tag, 60° C. extension | CCAGTGATGCAGCTG GCCCTAC [SEQ ID NO: 46] 60° C. extension |

TABLE 3-continued

| Snap shot assay | SNP# | rs# | location | Sequence of PCR primers and assay condition | Primer extension primers and condition |
|---|---|---|---|---|---|
| | 8 | rs4646437 | intron7 | TTATGATTTGGGTTATTCTAGGAGAC [SEQ ID NO: 9]<br>CCTGGAGCAATTCTAGTTTTCTCT [SEQ ID NO: 10]<br>Choice Tag, 60° C. extension | GGCAGGTCTATGCATAAGGAGCACC [SEQ ID NO: 47] |
| | 11 | rs28988604 | 3UTR | F: TGGTCATTGTAATCACTGTTGGC [SEQ ID NO: 11]<br>R: TTAAGTGTTCATTGCATCGAGAC [SEQ ID NO: 12]<br>Choice Tag, 60° C. extension | (T15)CAAACTGCTAGGATTACAGGC [SEQ ID NO: 48]<br>15 Ts were added at 5' end [SEQ ID NO: 49]<br>60° C. extension |
| | 12 | rs28969391 | 3'UTR | same as above | AAGCCTGGCCTACATGGT [SEQ ID NO: 50]<br>60° C. extension |
| | 13 | rs28371763 | 3UTR | same as above | (T4)GTGAGAGTGAGACTCAGTCTTAAAAA [SEQ ID NO: 51]<br>4 Ts were added at 5' end<br>60° C. extension |
| Note: SNP 11-13 can be multiplexed | | | | | |
| | 7 | rs2246709 | intron 7 | F: TTTAGCTATCAGCCCCCTGT [SEQ ID NO: 13]<br>R: TGAAGCCAGCAGAAGAAAGAA [SEQ ID NO: 14]<br>JumpStart RedTag, 60° C. extension | (T11)CAACCACTAATCAACTTTCTGC [SEQ ID NO: 52]<br>11 Ts were added at 5' end [SEQ ID NO: 53]<br>55° C. extension |
| | 9 | rs2242480 | intron 10 | F: GCTATGAAACCACGAGCAGTGT [SEQ ID NO: 15]<br>R: GGGAAGTGGTGAGGAGGC [SEQ ID NO: 16] | (T18)CCTCCCTCCTTCTCCATGTA [SEQ ID NO: 54]<br>18 Ts were added at 5' end [SEQ ID NO: 55]<br>55° C. extension |
| | 10 | rs3735451 | intron 12 | F: ATAGATGATGAATGCTCTCACTGTCC [SEQ ID NO: 17]<br>R: GGGATCTGCAACAGTTAAACAAG [SEQ ID NO: 18] | TTTTTTTGCCCATTACTCCAT [SEQ ID NO: 56]<br>55° C. extension |
| Note: SNP 7, 9 and 10 can be multiplexed | | | | | |
| Allele specific PCR assay | 1 | TGT ins | 11 kb upstream | common F: GCTCATAGAATCCTGGGCAT [SEQ ID NO: 19]<br>TGTwtR: CCTATCTAGCCATTAGAACCACATGT [SEQ ID NO: 20]<br>TGTinsR: CCTATCTAGCCATTAGAACCACATGTACA [SEQ ID NO: 21] | |
| | 4 | rs2687105 | intron 2 | snpF: GCTGCACCTTATGGGTGTGT [SEQ ID NO: 22]<br>wtF: GCTGCACCTTATGGGTGTGA [SEQ ID NO: 23]<br>common R: ATTGACCACCACTGTCTCATCTC [SEQ ID NO: 24] | |

TABLE 3-continued

Genotyping or AEI assays

| Snap shot assay | SNP# | rs# | location | Sequence of PCR primers and assay condition | Primer extension primers and condition |
|---|---|---|---|---|---|
| | 5 | rs28988579 | intron 4 | wtF: GTATAATGTTGAGTAAATGTGGTGAGTT [SEQ ID NO: 25]<br>snpF: GTATAATGTTGAGTAAAT-GTGGTGATTG [SEQ ID NO: 26]<br>common R: AAAGAACTGAAGGCTTCCCTC [SEQ ID NO: 27] | |
| | 6 | rs35599367 | intron 6 | wtF: GTGTCTCCATCACACCCTGC [SEQ ID NO: 28]<br>snpF: GTGTCTCCATCACACCCCGT [SEQ ID NO: 29]<br>common R: GGTGTTATCAGGTGCCAGTG [SEQ ID NO: 30] | |
| Primers for real-time PCR to quantitate mRNA | | | | primer sequence | |
| | | | CYP3A4 | F: CTCTCATCCCAGACTTGGCCA [SEQ ID NO: 31]<br>R: ACAGGCTGTTGACCATCATAAAAG [SEQ ID NO: 32] | |
| | | | PXR | F: CAAGCGGAAGAAAAGTGAACG [SEQ ID NO: 33]<br>R: CACAGATCTTTCCGGACCTG [SEQ ID NO: 34] | |
| | | | RXR | F: GAGCGGCAGCGTGGCAAGG [SEQ ID NO: 35]<br>R: GGCAAATGTTGGTGACAGGG [SEQ ID NO: 36] | |
| | | | HNF4a | F: ACATGGACATGGCCGACTAC [SEQ ID NO: 37]<br>R: CTCGAGGCACCGTAGTGTTT [SEQ ID NO: 38] | |
| | | | CAR | F: CACATGGGCACCATGTTTGA [SEQ ID NO: 39]<br>R: AAGGGCTGGTGATGGATGAA [SEQ ID NO: 40] | |
| | | | GADPH | F: ACTCCTCCACCTTTGACGCT [SEQ ID NO: 41]<br>R: GGTCCACCACCCTGTTGC [SEQ ID NO: 42] | |

Table 4: Multiplex PCR and Snapshot assay for CYP3A4 and CYP3A5 SNP genotyping. Column labeled "PCR primer sequence" discloses SEQ ID NOS 57-68, respectively, in order of appearance and column labeled "Primer extension primers" discloses SEQ ID NOS 69-75, respectively, in order of appearance.

TABLE 4

Multiplex PCR and Snapshot assay for CYP3A4 and CYP3A5 SNP genotyping

| SNP | PCR primer sequence | Primer extension primers | Final primer conc in snapshot reaction |
|---|---|---|---|
| TGT ins | F: GCCTGCATTTTATCTCTGTCTCGTGG [SEQ ID NO: 57]<br>R: GAAGGTGGGAAACAGCCAGATCAGA [SEQ ID NO: 58] | (T8)ATTCCCTATCTAGCCAT TAGAACCACA [SEQ ID NO: 69] | 20 nM |

TABLE 4-continued

Multiplex PCR and Snapshot assay for CYP3A4 and CYP3A5 SNP genotyping

| SNP | PCR primer sequence | Primer extension primers | Final primer conc in snapshot reaction |
|---|---|---|---|
| rs2740574 | F: AGAGCCATGACAGGGAATAAGACTAGA [SEQ ID NO: 59]<br><br>R: TGGGCTATGTGCATGGAGCTT [SEQ ID NO: 60] | (T15) AGGACAGCCATAGAGACAA GGGCA [SEQ ID NO: 70] | 50 nM |
| rs35599367 | F: CTGAAGCACAGTGCTTACCCAT [SEQ ID NO: 61]<br><br>R: GCCACAACATAGTAAACGAAGAAGGGCA [SEQ ID NO: 62] | CCAGTGATGCAGCTGGCCCT AC [SEQ ID NO: 71] | 80 nM |
| rs4987161 | same as above | (T20) GTTGAGAGAGTCGATGTTC ACTCCA [SEQ ID NO: 72] | 80 nM |
| rs28371759 | F: CTGTGATGCCCTACATTGATCTGATTTA CCTA [SEQ ID NO: 63]<br>R: CTGGGAAGTGGTGAGGAGGCATTTT [SEQ ID NO:64] | (T16) TCTCCTTTCAGCTCTGT CCGATC [SEQ ID NO: 73] | 60 nM |
| rs776746 | F: GTATGTACCACCCAGCTTAACGAATGCTC [SEQ ID NO: 65]<br><br>R: CACACAGGAGCCACCCAAGGC [SEQ ID NO:66] | TGTGGTCCAAACAGGGAAG AGATA [SEQ ID NO: 74] | 50 nM |
| rs1303343 | F: CCAATTCTGTTTCTTTCCTTCCAGGCA [SEQ ID NO: 67]<br><br>R: AACCAGCCTGGGTCAGGGTGAG [SEQ ID NO: 68]<br>Readymix Taq, 60° C. extension<br>Final primer cont for rs2740574 and rs35599367<br>is 300 nM, others are 150 nM<br>CYP3A4 PCR and sequencing primers<br>(ref sequence AF280107) | (T2) CATCTGTACCACGGCAT CATAGGTA [SEQ ID NO: 75]<br>55° C. extension | 15 nM |

Table 5: Primers and sequencing primers. PCR primers disclosed as SEQ ID NOS 76-95, respectively, in order of appearance and Sequencing primers disclosed as SEQ ID NOS 96-151, respectively, in order of appearance.

TABLE 5

PCR Primers and Sequencing Primers

| PCR primers Amplified region | Sequence 5'-3' | Sequencing primers Sequence 5'-3' |
|---|---|---|
| Promoter 1(49947 to 51960) | F: TTACAATAGCAATGACCTGGAACCAATCC [SEQ ID NO: 76]<br>R: GTGCAACCACAAACAATTAGGAACCTGT [SEQ ID NO: 77] | TTACAATAGCAATGACCTGGAACCA ATCC [SEQ ID NO: 96]<br>AATGGCAGGCACTGGAATT [SEQ ID NO: 97]<br><br>GTGCAACCACAAACAATTAGGAACC TGT [SEQ ID NO: 98] |

TABLE 5-continued

PCR Primers and Sequencing Primers

| PCR primers Amplified region | Sequence 5'-3' | Sequencing primers Sequence 5'-3' |
|---|---|---|
| Promoter 2 (51740 to 53696) | F: AGCCCAGGAGGCAGCAGTTGC [SEQ ID NO: 78] | AGCCCAGGAGGCAGCAGTTGC [SEQ ID NO: 99] |
| | R: GTCTTCCTAAAGGAGTGACTGTTTGCA TTATCAT [SEQ ID NO: 78] | TATGAAGTGAAGGCCAGAAACGA [SEQ ID NO: 100] |
| | | ACATGAAAAACAAAGCAACTCCAAC [SEQ ID NO: 101] |
| Promoter 3 (53408 to 55776) | F: TTGAGCCTGGGAGGCTGCG [SEQ ID NO: 80] | TTGAGCCTGGGAGGCTGCG [SEQ ID NO: 102] |
| | R: TAGCTTCTTCATTCGGTCTCAGTCCACTT [SEQ ID NO: 81] | ATGCTGGTTGCTGGTTTATTCTA [SEQ ID NO: 103] |
| | | GAGTTGGGCATGATGCCTTT [SEQ ID NO: 104] |
| Promoter 4 (55681 to 59417) | F: TCATTTTTGTAGAGCCTGAGGAGTGTCCA [SEQ ID NO: 82] | TCATTTTTGTAGAGCCTGAGGAGTGT CCA [SEQ ID NO: 105] |
| | R: GATTTACCTGCCCTACAAACTTTAGGAG GTGG [SEQ ID NO: 83] | CAAGAATGCTACCGGCACAA [SEQ ID NO: 106] |
| | | TGAATCCTGGCTCTGCTAAAGC [SEQ ID NO: 107] |
| | | ACCACTGGGAGCTTAAGTAAAGGG [SEQ ID NO: 108] |
| | | TCAAGTTTTCCCCTACTGAGAAGAAT [SEQ ID NO: 109] |
| Promoter 5 (59230 to 62323) | F: GTTACCTTCTGTGGAATTAAGTGGCAGA ACT [SEQ ID NO: 84] | GTTACCTTCTGTGGAATTAAGTGGCA GAACT [SEQ ID NO: 110] |
| | R: GACAGAGTTTCACCATGTTAGCCAGGC [SEQ ID NO: 85] | TTTTATCCCAGGGATTCCAG [SEQ ID NO: 111] |
| | | GAAATTCATCCCAACAAGCCACACC [SEQ ID NO: 112] |
| | | GACAGAGTTTCACCATGTTAGCCAGGC [SEQ ID NO: 113] |
| Promoter to intron 3 (61296 to 68200) | F: AGGGACCAGAGCCATGACAGGG [SEQ ID NO: 86] | AAGATGTTCAGGCCGGGC [SEQ ID NO: 114] |
| | R: TGACAAGAGCTTCATCCCAAGAGGC [SEQ ID NO: 87] | GTAGTGGAGGCTTCTCACATGTCA [SEQ ID NO: 115] |
| | | GCAGCCCAGGAGTCAGAAAC [SEQ ID NO: 116] |
| | | GGATCCATTTATACACACCATGCTT [SEQ ID NO: 117] |
| | | GATTCAGACCATATCACTGGCACT [SEQ ID NO: 118] |
| | | TCATTGCCGTCAGAGTTACTGTTATTA [SEQ ID NO: 119] |
| | | CCTGCTTCAATCCTCTCCGA [SEQ ID NO: 120] |
| | | GTGAAAACTCTGAGCAAGTGTTGTA ATT [SEQ ID NO: 121] |

TABLE 5-continued

PCR Primers and Sequencing Primers

| PCR primers Amplified region | Sequence 5'-3' | Sequencing primers Sequence 5'-3' |
|---|---|---|
| Intron 2 to intron 4 (667947 to 73642) | 2F2: TTTCATTGGCTTCGACTGTTTTCATCC [SEQ ID NO: 88] | TTTCATTGGCTTCGACTGTTTTCATCC [SEQ ID NO: 122] |
| | 2R2: ACAGGATGAAGTGGACGTGGAACCTT [SEQ ID NO: 89] | GGATCCCATGTGTCACCAGG [SEQ ID NO: 123] |
| | | CCCGTGTCCATGTGTTCTCA [SEQ ID NO: 124] |
| | | CTTCGTCAGATGGATAGATTGCAA [SEQ ID NO: 125] |
| | | GTTCTTCCATTTGTTTGTGTCCTCT [SEQ ID NO: 125] |
| | | TGCTGACTTGATCCTGGTGG [SEQ ID NO: 127] |
| | | TCTTAGTTATTCTTGTCTCCTGCTAGC [SEQ ID NO: 128] |
| | | TCTTTGTAGGTCTCTAAGAACTTGCTTTAT [SEQ ID NO: 129] |
| Intron 3 to intron 8 (73332 to 79586) | 3F2: ATTATGTAAAGTCAGGATCAAAGTCTGGCTTCC [SEQ ID NO: 90] | ATTATGTAAAGTCAGGATCAAAGTCTGGCTTCC [SEQ ID NO: 130] |
| | 3R2: TCCCTTCTGAGAATATGGCTCCTTGAAG [SEQ ID NO: 91] | TGGTGCCATGTTTGAAAGTTCTT [SEQ ID NO: 131] |
| | | ATGTGCTTTGATTTTGTGTGTTGAT [SEQ ID NO: 132] |
| | | CCACGTGGATAATTTGCATGTAA [SEQ ID NO: 133] |
| | | TTGAAAGAGTAAGTAGAAGCGCAGC [SEQ ID NO: 134] |
| | | TGAGCAGGGAGTATAGAGAATAAGGAT [SEQ ID NO: 135] |
| | | TCAATCTAGAGACCTCATACATTTTTAGCT [SEQ ID NO: 136] |
| | | GAGAAAACTAGAATTGCTCCAGGTAAA [SEQ ID NO: 137] |
| Intron 8 to intron 11 (79395 to 84596) | 4F: AAATGAAAGTCCCTATCAGGCCACCTG [SEQ ID NO: 92] | AAATGAAAGTCCCTATCAGGCCACCTG [SEQ ID NO: 138] |
| | 4R: TCTTTCTCCCCCACACCTCCATAGAATA [SEQ ID NO: 93] | TTGCAGCTACCTAATACATCTAACATCC [SEQ ID NO: 139] |
| | | GCTAGTGCCATTGAAGATCAATTTTA [SEQ ID NO: 140] |
| | | AATATTGGTCCCTTAAGTTCCCTCA [SEQ ID NO: 141] |
| | | ACATGGAGAAGGAGGGAGGAG [SEQ ID NO: 142] |
| | | GCTGACTCAGCTCTCCCCAC [SEQ ID NO: 143] |
| | | ACCAGTATGAGTTAGTCTCTGGAGCTC [SEQ ID NO: 144] |
| Intron 11 to intron 13 (84264 to 89410) | 5F: CATCCACAATTCCAACAACTTACGATGAAG [SEQ ID NO: 94] | CATCCACAATTCCAACAACTTACGATGAAG [SEQ ID NO: 145] |
| | 5R: CTATTTAGGCTCTGGCTGCTCTTGCAA [SEQ ID NO: 95] | ATTTCAATGACCAGCCCACAA [SEQ ID NO: 146] |
| | | CATTGGAATCACCAGGGAGC [SEQ ID NO: 147] |
| | | TTACTTCTCTGCTCTGTTATTGGATACTG |

TABLE 5-continued

PCR Primers and Sequencing Primers

| PCR primers Amplified region | Sequence 5'-3' | Sequencing primers Sequence 5'-3' |
|---|---|---|
| | | [SEQ ID NO: 148] CTCCCTGGCAATTTTCTTGC [SEQ ID NO: 149] TTACAAAGCATTATTGTCATTACTGCAT [SEQ ID NO: 150] CTGTGACTTTGCCCATTGTTTAGA [SEQ ID NO: 151] |

Sequencing CYP3A4: The region from ~10,000 bp upstream of transcription start site to the last exon (from 50013 to 89410 in AF280107, total length 39,397 bp) was sequenced in two liver samples that showed allele-specific RNA expression. PCR and sequencing primers are shown in Table 10.

CYP3A4 enzymatic activity assay: CYP3A4 activities were quantified from liver microsomes with testosterone as a probe as described (23).

Data analysis: Association between discrete variables and genotypes were analyzed with Helix-Tree software (Golden Helix, Bozeman Mont.). LD plots were generated using Haploview. Multiple linear regression analysis was used for testing genotype effects on RNA expression, enzyme activity, and statin dose requirement using SPSS or Minitab software.

Figure 3:
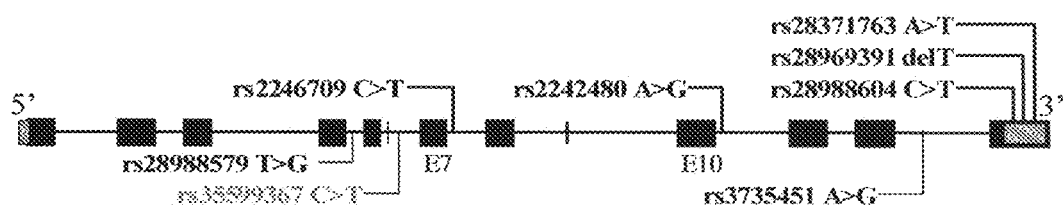
FIG. 3: Location and rs number of marker SNPs used for AEI measurements. Intron6 SNP rs35599367 [SEQ ID NO: 152] is in red.

Results:

Scanning for cis-acting CYP3A4 polymorphisms that affect mRNA levels:

Allelic mRNA expression of CYP3A4 was measured in human livers using 3 frequent 3' UTR marker SNPs (FIG. 3). Because of high CYP3A4 expression, 4 intronic SNPs also served to measure allelic expression of CYP3A4 hnRNA (24). Among 133 liver samples screened, 73 were heterozygous for at least one of the seven marker SNPs and therefore suitable for AEI measurement. Of the 73 samples, 7 were identified showing strong allelic expression imbalance (AEI), with the main allele expressed less than the minor allele (0.2 to 0.5 times), observed with both intronic and exonic marker SNPs (FIG. 1A). Therefore, a cis-acting polymorphism(s) in CYP3A4 affects both mRNA and hnRNA levels equally.

To search for responsible polymorphism(s), 13 CYP3A4 polymorphisms (Table 1) were genotyped and the association between allelic RNA ratios and genotype tested.

Figure 4:
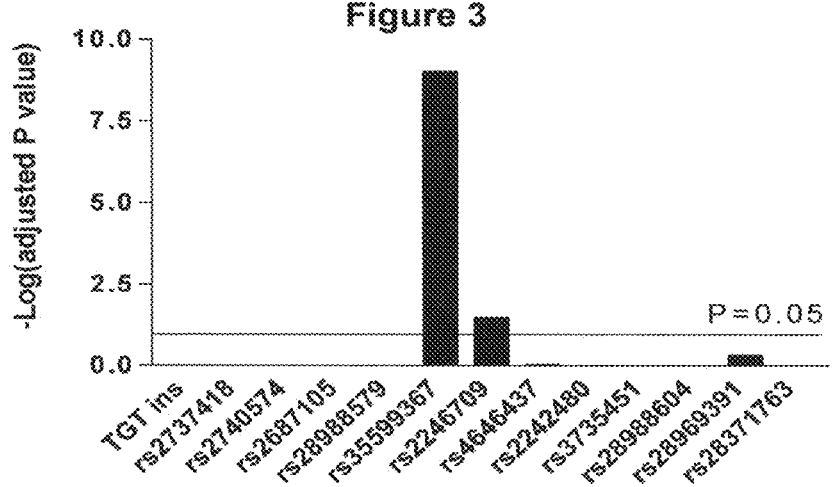
FIG. 4: Association between genotypes and allelic RNA expression imbalance (AEI). Only intron6 SNP rs35599367 [SEQ ID NO: 152] and much less strongly SNP rs2246709 associated with AEI with an adjusted P<0.05.
Figure 5:
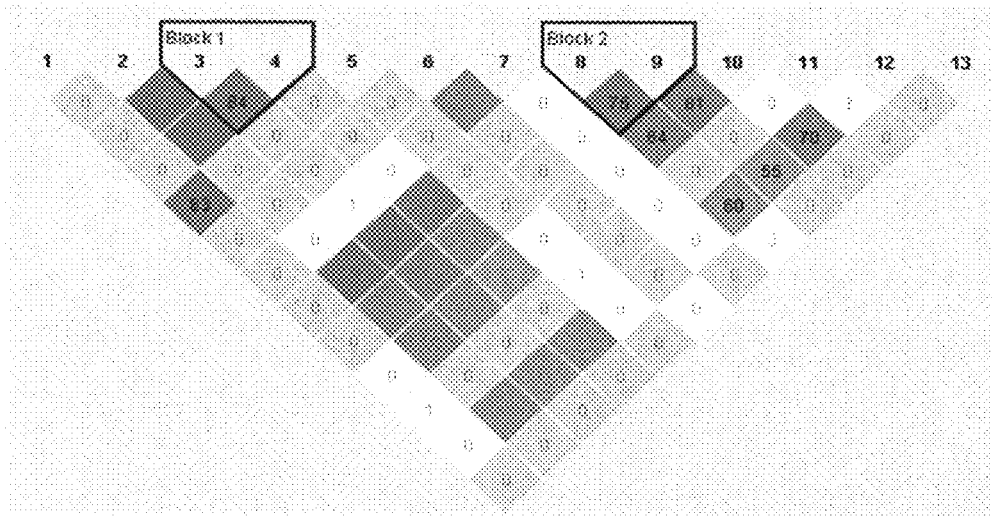
FIG. 5: LD plot for 13 polymorphisms in CYP3A4. Detailed SNP information is provided in Table 1. SNP6 is intron6 SNP rs35599367 [SEQ ID NO: 152], only partial LD with SNP 7 rs2246709.
Figure 6A:
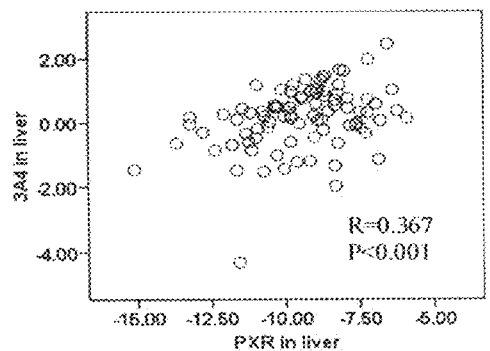
FIGS. 6A-6D: Correlation between mRNA expression of four transcription factors and CYP3A4 in human livers.
Figure 6B:
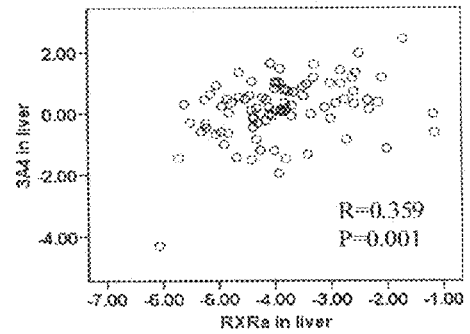
Figure 6C:
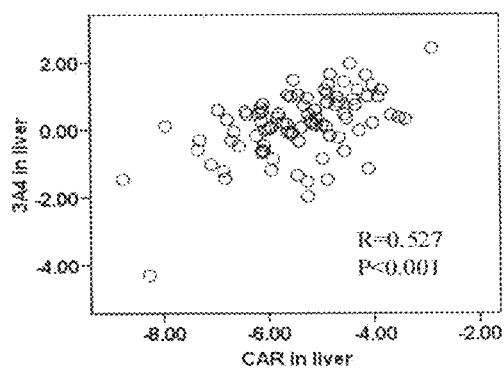
Figure 6D:
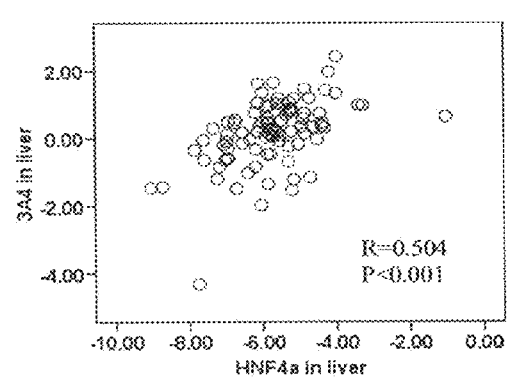

A single SNP (rs35599367 [SEQ ID NO: 152]) located in intron6 (C>T) showed highly significant association with AEI (adjusted p value $9.12 \times 10^{-10}$) (FIG. 4), while another SNP rs2246709 also scored with moderate significance (P=0.034), a likely result of partial linkage disequilibrium (LD) with the intron6 SNP (FIG. 5).

Other SNPs including previously identified promoter SNP rs2740574, TGT insertion, rs2737418, and rs4646437 did not show significant association (P>0.05). These results indicated that intron6 SNP is functional or in highly LD with a functional SNP.

Figure 1B:
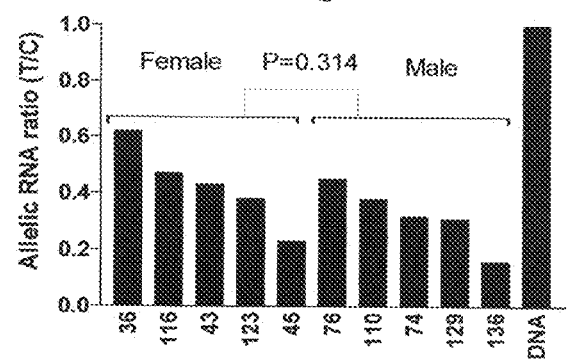

To test this further, intron6 SNP was used as a marker, and AEI was measured in 10 heterozygous samples, including 3 heterozygous only for intron6 SNP. All 10 samples showed AEI with allelic ratios (minor T allele/major C allele) ranging from 0.16 to 0.62 (FIG. 1B), with no differences between males and females (P=0.314). Therefore, the minor T allele of intron6 SNP is linked to reduced mRNA/hnRNA levels (the inverse allelic mRNA ratio of major C/minor T ranges from 1.6 to 6.25). The minor T allele is exclusively linked to the main CYP3A4 haplotype, except for low LD with rs2246709 (Table 6; LD plot FIG. 5).

Table 6: Haplotype structure and estimated frequency of 13 SNPs tested in livers. Detailed SNP information is provided in Table 1. In haplotype 5, the minor T allele of intron6 SNP (#6 from the left) is exclusively linked to the major haplotype 1 (in bold), whereas it has no detectable LD with any of the other SNPs.

TABLE 6

| Haplotype | | EM Frequency |
|---|---|---|
| 1 | D, G, A, A, T, C, T, C, G, A, C, T, A | 0.408 |
| 2 | D, G, A, A, T, C, C, C, G, A, C, T, A | 0.208 |
| 3 | D, G, G, T, T, C, T, T, A, G, C, G, A | 0.072 |
| 4 | D, G, A, A, T, C, T, T, A, G, C, G, A | 0.048 |
| 5 | D, G, A, A, T, T, C, C, G, A, C, T, A | 0.044 |
| 6 | D, G, A, A, T, C, C, T, A, G, C, G, A | 0.032 |
| 7 | I, G, A, A, G, C, T, C, G, A, C, T, A | 0.027 |
| 8 | D, G, A, A, T, C, T, T, G, A, C, T, T | 0.026 |
| 9 | D, T, G, T, T, C, C, T, A, G, C, G, A | 0.026 |
| 10 | D, G, A, A, T, C, T, C, G, G, T, G, A | 0.014 |

Sequencing of the entire CYP3A4 locus in two AEI-positive samples did not implicate any other polymorphisms that would have to be heterozygous in both samples, indicating that intron6 SNP is functional.

Intron6 SNP associates with decreased CYP3A4 mRNA level and enzyme activity in human livers:

Total CYP3A4 mRNA levels were measured in 93 liver samples. While mRNA levels did not differ between Caucasians and African Americans, females had –1.3 fold higher levels than males (95% CL 1.00-1.68, two-sided P=0.042) as reported (25). Livers with the main CC genotype of intron6 SNP had 1.71-fold (95% confidence interval (CI) 1.06-2.76) higher levels than CT/TT carriers (t test, two-sided p=0.028), with no interactions between genotypes and sex. To test the effect of CYP3A4 transcription factors (26-29), mRNA levels were also measured for pregnane X receptor (PXR, NR112), constitutive androstane receptor (CAR, NR113), retinoid receptor (RXRa), and hepatocyte nuclear factor (HNF4α1A). CYP3A4 mRNA expression positively correlated with all four transcription factors, as reported (26-29) (FIGS. 6A-6D).

Figure 2A:
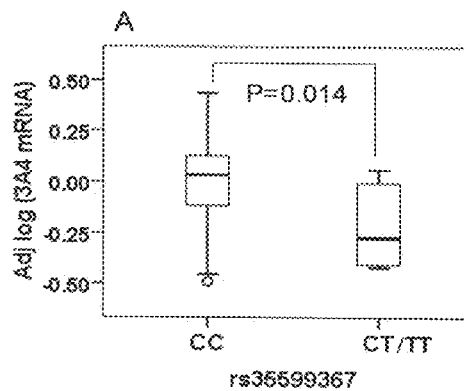
FIGS. 2A-2B: Box plot of CYP3A4 mRNA levels (FIG. 2A) and enzyme activity (FIG. 2B) in human liver samples, grouped by intron6 SNP genotype.

After adjusting for age and transcription factors, intron6 SNP remained significantly linked to CYP3A4 expression (1.67-fold CC over CT/TT (95%, CI 1.11-2.46, p=0.014) (FIG. 2A), showing that the genotype effect is independent of the transcription factors.

Figure 2B:
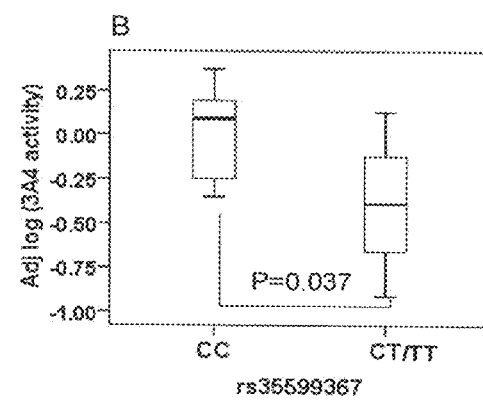

CYP3A4 enzyme activity (testosterone 6β-hydroxylation) in 23 livers was 2.46 fold higher for intron6 SNP CC than CT carriers, after adjusting for age (<15 child, >15 adult), sex, and use of inducers (phenobarbital, carbamazepine, nifedipine and dexamethasone) (two-sided p=0.037, 95% CI 1.07-5.62) (FIG. 2B).

Consistent with allelic mRNA expression, these results demonstrate that intron6 SNP decreases CYP3A4 mRNA and protein levels in vivo. In contrast, CYP3A4*1B, TGT insertion, rs2737418, and rs4646437 had no effect on total CYP3A4 mRNA level or enzyme activity (P>0.05).

Intron6 SNP (C>T) associates with statin dose requirement and lipid control outcome:

The in vivo effect of intron6 SNP was assessed as the dosage of CYP3A4-metabolized statins required for reaching a pre-determined LDL goal. Intron6 SNP was genotyped in 275 patients on stable doses of atorvastatin, lovastatin, and simvastatin, or the non-CYP3A4 substrates rosuvastatin and pravastatin. Additional SNPs in CYP3A4 (*1B rs2740574, TGT insertion, *17 rs4987161, and *18 rs28371759) and CYP3A5 (*3 rs776746 and *5 rs41303343) (Table 5) were also genotyped. Three SNPs deviated from Hardy-Weinberg equilibrium (HWE), because of different allele frequency in Caucasian and African American populations, in which all SNPs followed HWE when analyzed separately (Table 7).

ranging from 5 mg to 80 mg. The statins were either evaluated together, or each separately to account for potency differences. Patients on all statins were divided into low-dose (<20 mg, mean 16±5 mg) and high-dose (>40 mg, mean 53±19 mg) (P<0.001) groups. Baseline characteristics and lipid levels did not differ between low-and high-dose groups, except for maximum triglyceride and stable HDL levels (P<0.05) (Table 8). Table 8 shows the baseline characteristics of patients on CYP3A4-metabolized statins (atorvastatin, lovastatin and simvastatin).

TABLE 8

Baseline characteristics of patients on CYP3A4-metabolized statins (atorvastatin, lovastatin and simvastatin).

|  | All patient n = 237 | Low dose n = 121 | High dose n = 116 | P value |
|---|---|---|---|---|
| Dose (mg) | 34 ± 23 | 16 ± 5 | 53 ± 19 | <0.001 |
| Age | 62 ± 11 | 63 ± 13 | 62 ± 10 | 0.444 |
| Maximum LDL (mg/dl) | 105 ± 49 | 102 ± 52 | 108 ± 45 | 0.362 |
| Stable LDL (mg/dl) | 82 ± 33 | 85 ± 39 | 80 ± 24 | 0.297 |
| Minimum HDL (mg/dl) | 33 ± 10 | 34 ± 10 | 32 ± 9 | 0.141 |
| Stable HDL (mg/dl) | 35 ± 10 | 36 ± 10 | 33 ± 9 | 0.042* |
| Max Triglyceride (mg/dl) | 256 ± 430 | 196 ± 159 | 318 ± 590 | 0.043* |
| Stable Triglyceride (mg/dl) | 156 ± 106 | 145 ± 108 | 166 ± 104 | 0.159 |
| Max total Cholesterol (mg/dl) | 185 ± 79 | 175 ± 65 | 194 ± 91 | 0.085 |
| Stable Cholesterol (mg/dl) | 148 ± 41 | 149 ± 47 | 147 ± 35 | 0.650 |
| Male | 156/232 (67%) | 74/120 (62%) | 82/112 (73%) | 0.070 |
| White | 204/228 (89%) | 108/120 (90%) | 97/108 (89%) | 0.607 |

TABLE 7

SNPs tested in 275 patients.

|  |  |  | All Patients n = 275 | | White n = 240 | | Black and others n = 35 | |
|---|---|---|---|---|---|---|---|---|
| SNP | Alleles | Location | MAF | HWE P | MAF | HWE P | MAF | HWE P |
| TGT | TGT Del/Ins | CYP3A4 enhancer | 0.016 | 0.78 | 0.017 | 0.79 | 0.018 | 0.92 |
| rs2740574 | A > G | CYP3A4 promoter | 0.105 | 6.06E−07 | 0.054 | 0.71 | 0.350 | 0.77 |
| rs35599367 | C > T | CYP3A4 intron 6 | 0.047 | 0.061 | 0.052 | 0.08 | 0 | NA |
| rs4987161 | T > C | CYP3A4 exon 7 | 0 | NA | 0 | NA | 0 | NA |
| rs28371759 | T > C | CYP3A4 exon 10 | 0 | NA | 0 | NA | 0 | NA |
| rs776746 | G > A | CYP3A5 intron 3 | 0.138 | 2.81E−08 | 0.088 | 0.09 | 0.376 | 0.28 |
| rs1303343 | T Del/Ins | CYP3A5 exon 11 | 0.012 | 4.53E−06 | 0.008 | 0.95 | 0.055 | 0.76 |

The allele frequency of intron6 SNP is ~5%, consistent with that reported in NCBI database. Absence of CYP3A4 SNPs *17 and *18 is consistent with reported low allele frequency.

A subset of 237 patients were on CYP3A4-metabolized statins (atorvastatin, lovastatin, simvastatin) with doses The minor intron6 SNP T allele was significantly associated with a lower stable statin dose (odd ratios=3.80, P=0.005). None of the other SNPs were significant. Table 9 shows the association of CYP3A4/3A5 SNP genotypes with statins dose requirement and cholesterol control outcome. *P<0.05, **P<0.01.

TABLE 9

Association of CYP3A4/3A5 SNP genotypes with statins dose requirement and cholesterol control outcome.

| | Low dose vs high dose | | Goal vs not goal | |
|---|---|---|---|---|
| SNP | Minor allele odd ratio (95% CL) | P value | Minor allele odd ratio (95% CL) | P value |
| TGT | 0.31 (0.06~1.54) | 0.165 | 1.24 (0.24~6.50) | 0.794 |
| rs2740574 (*1B) | 1.30 (0.74~2.32) | 0.388 | 0.58 (0.32~1.05) | 0.083 |
| rs35599367 (intron 6) | 3.80 (1.38~10.35) | 0.005** | 3.49 (1.02~11.96) | 0.039* |
| rs776746 | 0.96 (0.57~1.63) | 0.902 | 0.65 (0.37~1.14) | 0.139 |
| rs41303343 | 0.94 (0.18~4.71) | 0.942 | 0.24 (0.04~1.34) | 0.097 |

*P < 0.05,
**P < 0.01.

Multiple linear regression analysis shows that the stable statin dose for intron6 T allele carriers was only 0.27 that for non T-carriers (P=0.019), after adjusting for maximum lipid levels (Table 10). Similar results were obtained when analyzing patients on atorvastain and simvastatin separately (Table 10). Therefore, intron6 SNP is linked to reduced statin dose requirement.

TABLE 10

CYP3A4 intron6 SNP genotypes and stable statin doses.

| Statins | N | Dose ratio (T carrier/ non-Tcarrier) | 95% confidence interval | P value |
|---|---|---|---|---|
| CYP3A4 substrates | 237 | 0.27 | 0.19~0.66 | 0.019* |
| Atorvastatin | 143 | 0.22 | 0.14~0.54 | 0.024* |
| Simvastatin | 85 | 0.6 | 0.37~0.97 | 0.042* |

*P < 0.05

For testing the association of intron6 SNP with cholesterol control outcome, 198 patients with available LDL data were divided into those who reached the cholesterol goal (LDL cholesterol<70 mg/dl; or 71-99 mg/dl with low/moderate risk; or 100-129 mg/dl with low risk) and those not at goal (>130 mg/dl; or 100-129 mg/dl with moderate/high risk; or 71-99 mg/dl with high risk) according to Adult Treatment Panel III Guidelines (30). Individuals bearing the T allele of intron6 SNP had a 3.5 fold higher chance of reaching goal cholesterol control than non T-carriers (P=0.039) (Table 2). In contrast, other SNPs did not show such associations.

Discussion of EXAMPLE I:

Example I shows that intron6 SNP rs35599367 [SEQ ID NO: 152] is significantly linked to reduced CYP3A4 mRNA expression and enzyme activity in human livers, and moreover, fully accounts for differences in allelic mRNA expression.

Since intron6 SNP is embedded in the main haplotype of CYP3A4, lacking substantial LD to any other SNPs, it had escaped detection by association studies using haplotype tag SNPs (14,15). None of the previously reported CYP3A4 SNPs, including promoter *1B, enhancer TGT insertion, enhancer rs2737418, and intron7 SNP rs4646437 had detectable effects on allelic mRNA expression, mRNA, and enzyme activity, arguing against a contribution of these SNPs to CYP3A4 variability.

The allele frequency of intron6 SNP in the examined cohort was ~5%, resulting in ~10% heterozygocity. Previously reported allele frequencies (35) were 0.043, 0.043, and 0.083, for African Americans, Chinese, and Caucasians, respectively, indicating that intron6 SNP allele frequency ranges from 4 to 8% in various ethnic groups.

A common molecular mechanism for an intronic SNP to alter mRNA levels is to affect RNA expression, elongation, splicing, or maturation. Since the allelic ratios were similar for mRNA and hnRNA in livers heterozygous for both exonic and intronic marker SNPs, splicing and mRNA turnover can be ruled out as main mechanisms. Moreover, CYP3A4 mRNA and hnRNA levels were shown to vary in parallel in human livers (36), arguing for an early event in expression and processing. For example, intron6 SNP could affect the folding of nascent RNA and hence elongation.

In silico RNA folding analysis shows that intron6 SNP promotes a loop-to-stem structural change (not shown), possibly impeding the binding of regulatory proteins.

Consistent with reduced expression of the minor allele, intron6 SNP was significantly associated with reduced stable dose requirements of statin drugs that are mainly metabolized by CYP3A4 (atorvastatin, lovastatin and simvastatin). Since statin doses are titrated to reach a desired LDL, this can be achieved at lower doses in carriers of the intron6 SNP T allele conveying reduced metabolism. In support of the inventors' belief, pharmacokinetics studies showed that inhibition of CYP3A4 activity drastically increased plasma concentrations of simvastatin and lovastatin (31,32), suggesting CYP3A4 activity is a major determinant of serum concentration of CYP3A4 metabolized statins.

The finding that patients carrying the intron6 T allele are also more likely to reach LDL goal may be related to insufficient dosage titration in subjects with normal CYP3A4 metabolism, or with lower fluctuations in statin levels between doses in T allele carriers. The previously identified CYP3A4 promoter SNP (*1B, −392 A>G) did not associate with lipid-lowering efficacy and safety of simvastin treatment (33), consistent with the results here showing this promoter SNP has no effect on hepatic mRNA expression. Further, the current results indicate that SNPs in CYP3A5 do not affect statin dose or treatment outcomes, consistent with reports that CYP3A5 does not play a major role in statin metabolism (34). Therefore, intron6 SNP is the only CYP3A polymorphism shown to affect statin therapy.

Even though CYP3A4 activity shows considerable interindividual variability, new drugs are often targeted for metabolism by CYP3A4, to avoid problems arising from null mutations in other drug metabolizing CYP enzymes, such as CYP2D6.

The results presented here show that a portion of the variability in CYP3A4 can be accounted for by intron6 SNP. The clinical relevance of this finding is demonstrated by the impact of intron6 SNP on the titrated dose of two statin drugs that depend on CYP3A4 for their elimination. Because CYP3A4 is involved in the metabolism of approximately half of all clinically used drugs, the intron6 SNP is now believed by the inventors herein to affect dosing requirements, response, and toxicity of numerous drugs, including anticancer agents with narrowly defined dosage regimens.

Therefore, CYP3A4 intron6 SNP is a valuable biomarker in clinical practice, and in drug discovery and development.

EXAMPLE II

The DNA isolated from cells can be used as positive human genomic reference controls (i.e., they have mutations present) or negative controls (i.e., they represent the normal or wild-type), in particular, for human CYP3A4 genes. This can ensure accurate and reliable clinical diagnostic testing for these genes.

The reference controls can be used, for example, in genotyping assays performed during clinical trials. Where the reference controls include a genetic variation typical of a patient who does not respond to therapy, the use of reference controls helps ensure that the genotyping assay used performs reliably such that non-responders are properly identified and data regarding the ineffectiveness of the investigative therapy for non-responders is properly identified. Similarly, where the reference controls include a genetic variation typical of a patient who metabolizes drugs at a different rate than normal patients (i.e., patients with mutant cytochrome P450 genes), the use of reference controls helps ensure the validity of the genetic variation so that these patients are properly identified and properly dosed and adverse drug reactions or ineffective therapies are avoided.

The reference controls can also be used in patient care. As with their use in clinical trials, it is essential that effective therapy is identified in a time-sensitive manner, so that the patient's condition is not worsened before appropriate therapy is initiated. It is also essential that appropriate dosing regimens are selected.

Accordingly, one aspect of the present invention relates to a method of testing a plurality of patients for their genetic predisposition to respond to a particular therapy. In this aspect, one or more reference controls are tested as "samples"—with known expected results. These controls can include a genetic variant associated with patients who show a predisposition to not respond to the therapy (positive controls) or can include a normal/wild type variant (negative controls), associated with patients who show a predisposition to respond to the therapy.

Thus, the reference controls can be used by testing laboratories to ensure that their diagnostics assays are performing correctly and identify the genetic variations that convey resistance to drug therapy or reduced metabolic state. To ensure that non-responders are properly identified, testing laboratories can include reference controls in each assay to determine the validity of the assay, and hence, patient results. The reference controls can be used at random, or at pre-determined intervals. In the same respect, testing laboratories can use the reference controls as panels to evaluate the accuracy of their laboratory staff.

Accordingly, another aspect of the present invention relates to a method of testing a plurality of patients for their genetic predisposition to show rapid or slowed metabolism, so that proper dosing regimens can be set. In this aspect, one or more samples that are tested are reference controls that include a genetic variant associated with patients having a predisposition to be "rapid" or "slow" metabolizers.

These polymorphisms are expressed in a number of phenotypes in the population such as, for example, a "poor" metabolizer, an "intermediate" metabolizer, an "extensive" metabolizer, and an "ultra-rapid" metabolizer. In certain situations, the "extensive" metabolizers can have at least one, and no more than two, normal functional alleles; the "intermediate" metabolizers can possess one reduced activity allele and one null allele; and, the "poor" metabolizers can carry two mutant alleles which result in complete loss of enzyme activity. In certain situations, the ultra-rapid metabolizers can carry multiple copies of functional alleles, and thus produce excess enzymatic activity. Thus, when certain drugs are administered, a "poor" metabolizer may not obtain a significant benefit from the drugs, but rather, experience exaggerated drug response and side effects when they receive standard doses. That is, if a metabolite is the active therapeutic moiety, "poor" metabolizer may show no therapeutic response. On the other hand, an "ultra-rapid" metabolizer may fail to respond to standard doses.

Various methods for pre-screening samples may be used. For example, biological samples can be pre-screened to ensure that they have the mutation of interest. Patient populations can be pre-screened, based on a variety of factors, to minimize the sample size needed to identify individuals that include the mutation. After performing an initial genomic screening on the samples to identify one or more samples which include the mutation of interest, the patients with these mutations can optionally be recalled to obtain additional biological material. This material can optionally be thoroughly sequenced to confirm the presence of the mutation of interest. The biological material can be immortalized, so it can provide a steady, on-demand source of the reference controls, or, alternatively, the cells themselves can be the reference controls. Various types of biological samples can be used, such as, but not limited to human genomic DNA present in any nucleic acid-containing sample of tissues, bodily fluids (for example, blood, serum, plasma, saliva, urine, tears, semen, vaginal secretions, lymph fluid, cerebrospinal fluid or mucosa secretions), individual cells or extracts of the such sources that contain the nucleic acid of the same, and subcellular structures such as mitochondria or chloroplasts, using protocols well established within the art.

In certain embodiments, the nucleic acid has been obtained from a human to be pre-screened for the presence of one or more genetic sequences that can be diagnostic for, or predispose the subject to, a medical condition or disease. As an alternative to prescreening patient populations, one can screen cell cultures commonly available for the genetic sequence of interest, and then expand and preserve the cell clones for future continuous supply There are a number of known genomic assay methods for which the reference control can be used in testing where most involve hybridizing a primer with a DNA sample that may or may not include a SNP of interest. A diagnostic primer and/or probe can be tagged to permit rapid identification. Once hybridization has occurred, the DNA can be amplified, and the tagged primer and/or probe are detected. The validated primers can be used to confirm the validity of reference controls. Once the reference controls are validated, they can be used in commercially available assays as a reference control, and can be used to validate primers that are designed for use in these or other assays to determine the presence or absence of a particular mutation. Thus, while exemplary assay methods are described herein, the invention is not so limited.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof. Therefore, it is intended that the invention not be limited to the particular embodiment disclosed herein contemplated for carrying out this invention, but that the invention will include all embodiments falling within the scope of the claims.

The citation of any reference herein is not an admission that such reference is available as prior art to the instant invention. Any publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

References

1. Danielson, P. B. (2002) *Curr Drug Metab* 3, 561-597.
2. Ozdemir, V., Kalow, W., Tang, B. K., Paterson, A. D., Walker, S. E., Endrenyi, L., and Kashuba, A. D. (2000) *Pharmacogenetics* 10, 373-388.
3. Rebbeck, T. R., Jaffe, J. M., Walker, A. H., Wein, A. J., and Malkowicz, S. B. (1998) *J Natl Cancer Inst* 90, 1225-1229.
4. Westlind, A., Lofberg, L., Tindberg, N., Andersson, T. B., and Ingelman-Sundberg, M. (1999) *Biochem Biophys Res Commun* 259, 201-205.
5. Wojnowski, L., and Kamdem, L. K. (2006) *Expert Opin Drug Metab Toxicol* 2, 171-182.
6. Lamba, J. K., Lin, Y. S., Thummel, K., Daly, A., Watkins, P. B., Strom, S., Zhang, J., and Schuetz, E. G. (2002) *Pharmacogenetics* 12, 121-132.
7. Garcia-Martin, E., Martinez, C., Pizarro, R. M., Garcia-Gamito, F. J., Gullsten, H., Raunio, H., and Agundez, J. A. (2002) *Clin Pharmacol Ther* 71, 196-204.
8. Amirimani, B., Walker, A. H., Weber, B. L., and Rebbeck, T. R. (1999) *J Natl Cancer Inst* 91, 1588-1590.
9. Spurdle, A. B., Goodwin, B., Hodgson, E., Hopper, J. L., Chen, X., Purdie, D. M., McCredie, M. R., Giles, G. G., Chenevix-Trench, G., and Liddle, C. (2002) *Pharmacogenetics* 12, 355-366.
10. Ball, S. E., Scatina, J., Kao, J., Ferron, G. M., Fruncillo, R., Mayer, P., Weinryb, I., Guida, M., Hopkins, P. J., Warner, N., and Hall, J. (1999) *Clin Pharmacol Ther* 66, 288-294.
11. Zeigler-Johnson, C., Friebel, T., Walker, A. H., Wang, Y., Spangler, E., Panossian, S., Patacsil, M., Aplenc, R., Wein, A. J., Malkowicz, S. B., and Rebbeck, T. R. (2004) *Cancer Res* 64, 8461-8467.
12. Kuehl, P., Zhang, J., Lin, Y., Lamba, J., Assem, M., Schuetz, J., Watkins, P. B., Daly, A., Wrighton, S. A., Hall, S. D., Maurel, P., Relling, M., Brimer, C., Yasuda, K., Venkataramanan, R., Strom, S., Thummel, K., Boguski, M. S., and Schuetz, E. (2001) *Nat Genet* 27, 383-391.
13. Matsumura, K., Saito, T., Takahashi, Y., Ozeki, T., Kiyotani, K., Fujieda, M., Yamazaki, H., Kunitoh, H., and Kamataki, T. (2004) *Mol Pharmacol* 65, 326-334.
14. Perera, M. A., Thirumaran, R. K., Cox, N. J., Hanauer, S., Das, S., Brimer-Cline, C., Lamba, V., Schuetz, E. G., Ratain, M. J., and Di Rienzo, A. (2008) *Pharmacogenomics J.*
15. Schirmer, M., Rosenberger, A., Klein, K., Kulle, B., Toliat, M. R., Nurnberg, P., Zanger, U. M., and Wojnowski, L. (2007) *Pharmacogenomics* 8, 443-453.
16. Wang, D., Johnson, A. D., Papp, A. C., Kroetz, D. L., and Sadee, W. (2005) *Pharmacogenet Genomics* 15, 693-704.
17. Pinsonneault, J., Nielsen, C. U., and Sadee, W. (2004) *J Pharmacol Exp Ther* 311, 1088-1096.
18. Miller, S. A., Dykes, D. D., and Polesky, H. F. (1988) *Nucleic Acids Res* 16, 1215
19. Dai, Z., Papp, A. C., Wang, D., Hampel, H., and Sadee, W. (2008) *BMC Med Genomics* 1, 24.
20. Papp, A. C., Pinsonneault, J. K., Cooke, G., and Sadee, W. (2003) *Biotechniques* 34, 1068-1072.
21. Wang, D., Papp, A. C., Binkley, P. F., Johnson, J. A., and Sadee, W. (2006) *Pharmacogenet Genomics* 16, 735-745.
22. Leeder, J. S., Gaedigk, R., Marcucci, K. A., Gaedigk, A., Vyhlidal, C. A., Schindel, B. P., and Pearce, R. E. (2005) *J Pharmacol Exp Ther* 314, 626-635.
23. Kolwankar, D., Vuppalanchi, R., Ethell, B., Jones, D. R., Wrighton, S. A., Hall, S. D., and Chalasani, N. (2007) *Clin Gastroenterol Hepatol* 5, 388-393.
24. Hirota, T., Ieiri, I., Takane, H., Maegawa, S., Hosokawa, M., Kobayashi, K., Chiba, K., Nanba, E., Oshimura, M., Sato, T., Higuchi, S., and Otsubo, K. (2004) *Hum Mol Genet* 13, 2959-2969.
25. Wolbold, R., Klein, K., Burk, O., Nussler, A. K., Neuhaus, P., Eichelbaum, M., Schwab, M., and Zanger, U. M. (2003) *Hepatology* 38, 978-988.
26. Vyhlidal, C. A., Gaedigk, R., and Leeder, J. S. (2006) *Drug Metab Dispos* 34, 131-137.
27. Goodwin, B., Redinbo, M. R., and Kliewer, S. A. (2002) *Annu Rev Pharmacol Toxicol* 42, 1-23.
28. He, P., Court, M. H., Greenblatt, D. J., and von Moltke, L. L. (2006) *J Clin Pharmacol* 46, 1356-1369.
29. Lamba, J., Lamba, V., and Schuetz, E. (2005) *Curr Drug Metab* 6, 369-383.
30. Grundy, S. M., Cleeman, J. I., Merz, C. N., Brewer, H. B., Jr., Clark, L. T., Hunninghake, D. B., Pasternak, R. C., Smith, S. C., Jr., and Stone, N. J. (2004) *J Am Coll Cardiol* 44, 720-732.
31. Neuvonen, P. J., Kantola, T., and Kivisto, K. T. (1998) *Clin Pharmacol Ther* 63, 332-341.
32. Jalava, K. M., Olkkola, K. T., and Neuvonen, P. J. (1997) *Clin Pharmacol Ther* 61, 410-415.
33. Fiegenbaum, M., da Silveira, F. R., Van der Sand, C. R., Van der Sand, L. C., Ferreira, M. E., Pires, R. C., and Hutz, M. H. (2005) *Clin Pharmacol Ther* 78, 551-558.
34. Park, J. E., Kim, K. B., Bae, S. K., Moon, B. S., Liu, K. H., and Shin, J. G. (2008) *Xenobiotica* 38, 1240-1251.
35. Thompson, E. E., Kuttab-Boulos, H., Witonsky, D., Yang, L., Roe, B. A., and Di Rienzo, A. (2004) *Am J Hum Genet* 75, 1059-1069.
36. Rodriguez-Antona, C., Sayi, J. G., Gustafsson, L. L., Bertilsson, L., and Ingelman-Sundberg, M. (2005) *Biochem Biophys Res Commun* 338, 299-305.

What is claimed is:

1. A method of administering a statin dose to a human, comprising:
   obtaining a nucleic acid-containing test sample from a human, wherein the human is in need of statin therapy;
   conducting at least one genotyping assay of the sample so as to obtain at least the genotype data at position rs35599367 of CYP3A4 in the sample, wherein the at least one genotyping assay comprises hybridizing a tagged primer to DNA in the nucleic acid-containing test sample, amplifying the hybridized DNA and detecting the tagged primer;
   detecting a T allele at position rs35599367 of CYP3A4; and administering a statin dose to the human comprising a TT or TC genotype at position rs35599367 of CYP3A4 of less than 20 mg per day wherein the statin administered is a statin that depends on CYP3A4 for elimination.

2. The method of claim 1, which further comprises a step of predicting cholesterol control outcome.

3. The method of claim 1, which further comprises identifying at least one additional biomarker of statin metabolism.

4. The method of claim 1, wherein said nucleic acid is a nucleic acid extract from a biological sample from said human.

5. The method of claim 4, in which said sample is blood, saliva, or buccal cells.

6. A method of administering a statin dose to a human, comprising:
   obtaining a nucleic acid-containing test sample from a human, wherein the human is in need of statin therapy;
   conducting at least one genotyping assay of the sample so as to obtain at least the genotype data at position rs35599367 of CYP3A4 in the sample, wherein the at least one genotyping assay comprises hybridizing a tagged primer to DNA in the nucleic acid-containing test sample, amplifying the hybridized DNA, and detecting the tagged primer;
   detecting a C allele at position rs35599367 of CYP3A4; and
   administering a statin dose to the human comprising a CC genotype at position rs35599367 of CYP3A4 of more than 40 mg per day, wherein the statin administered is a statin that depends on CYP3A4 for elimination.

7. The method of claim 6, which further comprises a step of predicting cholesterol control outcome.

8. The method of claim 6, which further comprises identifying at least one additional biomarker of statin metabolism.

9. The method of claim 6, wherein said nucleic acid is a nucleic acid extract from a biological sample from said human.

10. The method of claim 9, in which said sample is blood, saliva, or buccal cells.

11. The method of claim 1, wherein one or more statins are given, and the one or more statins is selected from the group consisting of atorvastatin, lovastatin, and simvastatin.

12. The method of claim 6, wherein one or more statins are given, and the one or more statins is selected from the group consisting of atorvastatin, lovastatin, and simvastatin.

* * * * *

SEQUENCE LISTING

<160> NUMBER OF SEQ ID NOS: 152

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
gaacttgctg accctctgct tt                                              22

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tagcaagcca cagacagca                                                  19

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
agagccatga cagggaataa gactaga                                         27

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tgggctatgt gcatggagct t                                               21

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tttcctttcc aatctgtatg cc                                              22

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aaagaactga aggcttccct c                                               21

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ctgaagcaca gtgcttaccc at    22

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggtgccagtg atgcagct    18

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ttatgatttg ggttattcta ggagac    26

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cctggagcaa ttctagtttt ctct    24

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tggtcattgt aatcactgtt ggc    23

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ttaagtgttc attgcatcga gac    23

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 13
tttagctatc agccccctgt                                                   20

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tgaagccagc agaagaaaga a                                                 21

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gctatgaaac cacgagcagt gt                                                22

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gggaagtggt gaggaggc                                                     18

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
atagatgatg aatgctctca ctgtcc                                            26

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gggatctgca acagttaaac aag                                               23

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
```
gctcatagaa tcctgggcat                                                    20

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cctatctagc cattagaacc acatgt                                             26

<210> SEQ ID NO 21
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cctatctagc cattagaacc acatgtaca                                          29

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gctgcacctt atgggtgtgt                                                    20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gctgcacctt atgggtgtga                                                    20

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
attgaccacc actgtctcat ctc                                                23

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gtataatgtt gagtaaatgt ggtgagtt                              28

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gtataatgtt gagtaaatgt ggtgattg                              28

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
aaagaactga aggcttccct c                                     21

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gtgtctccat cacaccctgc                                       20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gtgtctccat cacaccccgt                                       20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ggtgttatca ggtgccagtg                                       20

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ctctcatccc agacttggcc a                                     21

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
acaggctgtt gaccatcata aaag                                          24

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
caagcggaag aaaagtgaac g                                             21

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
cacagatctt tccggacctg                                               20

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 35
gagcggcagc gtggcaagg                                                19

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
ggcaaatgtt ggtgacaggg                                               20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
acatggacat ggccgactac                                               20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ctcgaggcac cgtagtgttt                                                20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
cacatgggca ccatgtttga                                                20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
aagggctggt gatggatgaa                                                20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
actcctccac ctttgacgct                                                20

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ggtccaccac cctgttgc                                                  18

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
cattctcctt taacctgttg acga                                           24

```
<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
aggacagcca tagagacaag ggca                                          24

<210> SEQ ID NO 45
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
agtataatgt tgagtaaatg tggtgaat                                      28

<210> SEQ ID NO 46
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ccagtgatgc agctggccct ac                                            22

<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ggcaggtcta tgcataagga gcacc                                         25

<210> SEQ ID NO 48
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
tttttttttt tttttcaaac tgctaggatt acaggc                             36

<210> SEQ ID NO 49
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
tttttttttt ttttt                                                    15

<210> SEQ ID NO 50
```

```
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
aagcctggcc tacatggt                                                    18

<210> SEQ ID NO 51
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ttttgtgaga gtgagactca gtcttaaaaa                                       30

<210> SEQ ID NO 52
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
tttttttttt tcaaccacta atcaactttc tgc                                   33

<210> SEQ ID NO 53
<211> LENGTH: 11
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
tttttttttt t                                                           11

<210> SEQ ID NO 54
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
tttttttttt ttttttttcc tccctccttc tccatgta                              38

<210> SEQ ID NO 55
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
tttttttttt tttttttt                                                    18

<210> SEQ ID NO 56
<211> LENGTH: 21
```

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
tttttttgcc cattactcca t                                         21

<210> SEQ ID NO 57
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
gcctgcattt tatctctgtc tcgtgg                                    26

<210> SEQ ID NO 58
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gaaggtggga aacagccaga tcaga                                     25

<210> SEQ ID NO 59
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
agagccatga cagggaataa gactaga                                   27

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
tgggctatgt gcatggagct t                                         21

<210> SEQ ID NO 61
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
ctgaagcaca gtgcttaccc at                                        22

<210> SEQ ID NO 62
<211> LENGTH: 28
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 62
gccacaacat agtaaacgaa gaagggca                                              28

<210> SEQ ID NO 63
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
ctgtgatgcc ctacattgat ctgatttacc ta                                        32

<210> SEQ ID NO 64
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
ctgggaagtg gtgaggaggc atttt                                                25

<210> SEQ ID NO 65
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
gtatgtacca cccagcttaa cgaatgctc                                            29

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
cacacaggag ccacccaagg c                                                    21

<210> SEQ ID NO 67
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
ccaattctgt ttctttcctt ccaggca                                              27

<210> SEQ ID NO 68
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 68
aaccagcctg ggtcagggtg ag                                              22

<210> SEQ ID NO 69
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69 tttttttttat tccctatcta gccattagaa ccaca                               35

<210> SEQ ID NO 70
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
tttttttttt tttttaggac agccatagag acaagggca                            39

<210> SEQ ID NO 71
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
ccagtgatgc agctggccct ac                                              22

<210> SEQ ID NO 72
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
tttttttttt tttttttttt gttgagagag tcgatgttca ctcca                     45

<210> SEQ ID NO 73
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
tttttttttt tttttttctc ctttcagctc tgtccgatc                            39

<210> SEQ ID NO 74
<211> LENGTH: 24
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 74
tgtggtccaa acagggaaga gata                                              24

<210> SEQ ID NO 75
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
ttcatctgta ccacggcatc ataggta                                           27

<210> SEQ ID NO 76
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
ttacaatagc aatgacctgg aaccaatcc                                         29

<210> SEQ ID NO 77
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
gtgcaaccac aaacaattag gaacctgt                                          28

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
agcccaggag gcagcagttg c                                                 21

<210> SEQ ID NO 79
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
gtcttcctaa aggagtgact gtttgcatta tcat                                   34

<210> SEQ ID NO 80
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 80
ttgagcctgg gaggctgcg                                                19

<210> SEQ ID NO 81
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
tagcttcttc attcggtctc agtccactt                                     29

<210> SEQ ID NO 82
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
tcatttttgt agagcctgag gagtgtcca                                     29

<210> SEQ ID NO 83
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
gatttacctg ccctacaaac tttaggaggt gg                                 32

<210> SEQ ID NO 84
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
gttaccttct gtggaattaa gtggcagaac t                                  31

<210> SEQ ID NO 85
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
gacagagttt caccatgtta gccaggc                                       27

<210> SEQ ID NO 86
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
agggaccaga gccatgacag gg                                           22

<210> SEQ ID NO 87
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
tgacaagagc ttcatcccaa gaggc                                        25

<210> SEQ ID NO 88
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
tttcattggc ttcgactgtt ttcatcc                                      27

<210> SEQ ID NO 89
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
acaggatgaa gtggacgtgg aacctt                                       26

<210> SEQ ID NO 90
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
attatgtaaa gtcaggatca aagtctggct tcc                               33

<210> SEQ ID NO 91
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
tcccttctga gaatatggct ccttgaag                                     28

<210> SEQ ID NO 92
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 92
aaatgaaagt ccctatcagg ccacctg                                          27

<210> SEQ ID NO 93
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
tctttctccc ccacacctcc atagaata                                         28

<210> SEQ ID NO 94
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
catccacaat tccaacaact tacgatgaag                                       30

<210> SEQ ID NO 95
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
ctatttaggc tctggctgct cttgcaa                                          27

<210> SEQ ID NO 96
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
ttacaatagc aatgacctgg aaccaatcc                                        29

<210> SEQ ID NO 97
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
aatggcaggc actggaatt                                                   19

<210> SEQ ID NO 98
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
```
gtgcaaccac aaacaattag gaacctgt                                            28

<210> SEQ ID NO 99
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
agcccaggag gcagcagttg c                                                   21

<210> SEQ ID NO 100
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
tatgaagtga aggccagaaa cga                                                 23

<210> SEQ ID NO 101
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
acatgaaaaa caaagcaact ccaac                                               25

<210> SEQ ID NO 102
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
ttgagcctgg gaggctgcg                                                      19

<210> SEQ ID NO 103
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
atgctggttg ctggtttatt cta                                                 23

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
gagttgggca tgatgccttt                                              20

<210> SEQ ID NO 105
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
tcatttttgt agagcctgag gagtgtcca                                    29

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
caagaatgct accggcacaa                                              20

<210> SEQ ID NO 107
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
tgaatcctgg ctctgctaaa gc                                           22

<210> SEQ ID NO 108
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
accactggga gcttaagtaa aggg                                         24

<210> SEQ ID NO 109
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
tcaagttttc ccctactgag aagaat                                       26

<210> SEQ ID NO 110
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
gttaccttct gtggaattaa gtggcagaac t                                 31

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
ttttatccca gggattccag                                              20

<210> SEQ ID NO 112
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
gaaattcatc ccaacaagcc acacc                                        25

<210> SEQ ID NO 113
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
gacagagttt caccatgtta gccaggc                                      27

<210> SEQ ID NO 114
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
aagatgttca ggccgggc                                                18

<210> SEQ ID NO 115
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
gtagtggagg cttctcacat gtca                                         24

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
gcagcccagg agtcagaaac                                              20

<210> SEQ ID NO 117
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
ggatccattt atacacacca tgctt                                           25

<210> SEQ ID NO 118
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
gattcagacc atatcactgg cact                                            24

<210> SEQ ID NO 119
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
tcattgccgt cagagttact gttatta                                         27

<210> SEQ ID NO 120
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
cctgcttcaa tcctctccga                                                 20

<210> SEQ ID NO 121
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
gtgaaaactc tgagcaagtg ttgtaatt                                        28

<210> SEQ ID NO 122
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
tttcattggc ttcgactgtt ttcatcc                                         27

<210> SEQ ID NO 123
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 123
ggatcccatg tgtcaccagg          20

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 124
cccgtgtcca tgtgttctca          20

<210> SEQ ID NO 125
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 125
cttcgtcaga tggatagatt gcaa          24

<210> SEQ ID NO 126
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 126
gttcttccat ttgtttgtgt cctct          25

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 127
tgctgacttg atcctggtgg          20

<210> SEQ ID NO 128
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 128
tcttagttat ttcttgtctc ctgctagc          28

<210> SEQ ID NO 129

```
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
tctttgtagg tctctaagaa cttgctttat                                     30

<210> SEQ ID NO 130
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
attatgtaaa gtcaggatca aagtctggct tcc                                 33

<210> SEQ ID NO 131
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
tggtgccatg tttgaaagtt ctt                                            23

<210> SEQ ID NO 132
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
atgtgctttg attttgtgtg ttgat                                          25

<210> SEQ ID NO 133
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
ccacgtggat aatttgcatg taa                                            23

<210> SEQ ID NO 134
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
ttgaaagagt aagtagaagc gcagc                                          25

<210> SEQ ID NO 135
<211> LENGTH: 27
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
tgagcaggga gtatagagaa taaggat                                              27

<210> SEQ ID NO 136
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
tcaatctaga gacctcatac atttttagct                                           30

<210> SEQ ID NO 137
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
gagaaaacta gaattgctcc aggtaaa                                              27

<210> SEQ ID NO 138
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
aaatgaaagt ccctatcagg ccacctg                                              27

<210> SEQ ID NO 139
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
ttgcagctac ctaatacatc taacatcc                                             28

<210> SEQ ID NO 140
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
gctagtgcca ttgaagatca atttta                                               26

<210> SEQ ID NO 141
<211> LENGTH: 25
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 141
aatattggtc ccttaagttc cctca                                          25

<210> SEQ ID NO 142
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
acatggagaa ggagggagga g                                              21

<210> SEQ ID NO 143
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
gctgactcag ctctccccac                                                20

<210> SEQ ID NO 144
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
accagtatga gttagtctct ggagctc                                        27

<210> SEQ ID NO 145
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
catccacaat tccaacaact tacgatgaag                                     30

<210> SEQ ID NO 146
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
atttcaatga ccagcccaca a                                              21

<210> SEQ ID NO 147
<211> LENGTH: 20
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 147
cattggaatc accagggagc                                                   20

<210> SEQ ID NO 148
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
ttacttctct gctctgttat tggatactg                                         29

<210> SEQ ID NO 149
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
ctccctggca attttcttgc                                                   20

<210> SEQ ID NO 150
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
ttacaaagca ttattgtcat tactgcat                                          28

<210> SEQ ID NO 151
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
ctgtgacttt gcccattgtt taga                                              24

<210> SEQ ID NO 152
<211> LENGTH: 52
<212> TYPE: DNA
<213> ORGANISM: Homo sapiens

<400> SEQUENCE: 152
cagttcagtg tctccatcac acccagygta gggccagctg catcactggc ac               52
```